US012082964B2

(12) United States Patent
Koehler et al.

(10) Patent No.: US 12,082,964 B2
(45) Date of Patent: Sep. 10, 2024

(54) DETECTOR FOR A DARK-FIELD, PHASE-CONTRAST AND ATTENUATION INTERFEROMETRIC IMAGING SYSTEM

(71) Applicant: KONINKLIJKE PHILIPS N.V., Eindhoven (NL)

(72) Inventors: Thomas Koehler, Norderstedt (DE); Herfried Karl Wieczorek, Aachen (DE); Gereon Vogtmeier, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 278 days.

(21) Appl. No.: 17/765,520

(22) PCT Filed: Sep. 16, 2020

(86) PCT No.: PCT/EP2020/075798
§ 371 (c)(1),
(2) Date: Mar. 31, 2022

(87) PCT Pub. No.: WO2021/063674
PCT Pub. Date: Apr. 8, 2021

(65) Prior Publication Data
US 2022/0338827 A1     Oct. 27, 2022

(30) Foreign Application Priority Data
Oct. 1, 2019   (EP) ...................................... 19200734

(51) Int. Cl.
*A61B 6/00*     (2024.01)
(52) U.S. Cl.
CPC .................... *A61B 6/484* (2013.01)

(58) Field of Classification Search
CPC ..... A61B 6/484; A61B 6/4035; A61B 6/4291; A61B 6/4208; A61B 6/4241; A61B 6/4266; G21K 2207/005
See application file for complete search history.

(56) References Cited

U.S. PATENT DOCUMENTS 10,573,690 B2   2/2020   Lifka
10,679,762 B2   6/2020   Koehler
(Continued)

FOREIGN PATENT DOCUMENTS

JP    2004151007 A    5/2004
WO   WO0127656 A1    4/2001
WO   WO2017212000 A1  12/2017

OTHER PUBLICATIONS

PCT International Search Report, International application No. PCT/EP2020/075798, Dec. 21, 2020.
(Continued)

*Primary Examiner* — Kiho Kim
(74) *Attorney, Agent, or Firm* — Larry Liberchuk

(57) ABSTRACT

A detector for a dark-field and/or phase-contrast interferometric imaging system comprises pixels, first detector arrays, second detector arrays, and a processor. For each pixel, each of the first and second detector arrays is configured to detect a cumulative charge associated with fingers of the respective detector array. For each pixel, the processor is configured to assign an X-ray interaction event to either the first detector array or the second detector array based on the detector array that has the highest cumulative charge.

15 Claims, 4 Drawing Sheets

(56) References Cited

U.S. PATENT DOCUMENTS

| | | |
|---|---|---|
| 2010/0246765 A1 | 9/2010 | Murakoshi |
| 2010/0246767 A1 | 9/2010 | Tanabe |
| 2013/0287175 A1 | 10/2013 | Nagai |
| 2018/0252821 A1 | 9/2018 | Svensson |
| 2019/0025440 A1 | 1/2019 | Steadman Booker |
| 2019/0304616 A1* | 10/2019 | Koehler ................ A61B 6/484 |

OTHER PUBLICATIONS

Weitkamp T. et al., "X-Ray Phase Imaging with a Grating Interferometer", Optics Express, vol. 13, No. 16, pp. 6296-6304, Aug. 2005.

* cited by examiner

DETECTOR FOR A DARK-FIELD, PHASE-CONTRAST AND ATTENUATION INTERFEROMETRIC IMAGING SYSTEM

FIELD OF THE INVENTION

The present invention relates to a detector for a dark-field, and/or phase-contrast interferometric imaging system and that can also be used for attenuation image data acquisition, and relates to an X-ray imaging system having such a detector.

BACKGROUND OF THE INVENTION

Grating-based Dark-field X-ray (DAX) and phase-contrast (gbPC) X-ray imaging (both radiography and computed tomography) are new X-ray imaging modalities, providing for the simultaneously images of the linear attenuation coefficient, the electron density, and the small angle scattering (i.e., an image obtained from the dark-field signal). The linear attenuation coefficient can also be simultaneously acquired, and thus dark-field, phase-contrast and attenuation images can be determined. X-ray dark-field and phase-contrast are two new imaging modalities that have shown the potential to increase significantly the diagnostic accuracy for soft-tissue imaging. One of the areas that has been identified to likely benefit most from these two new imaging modalities is chest radiography. It has been shown for example that X-ray dark-field information could significantly help diagnose such pulmonary disorders as chronic obstructive pulmonary disease (COPD) or pulmonary fibrosis, lung cancer etc.

For the acquisition of these new imaging modalities a two (Talbot type) or three-grating (Talbot-Lau type) interferometer is introduced into the X-ray beam, normally termed G0, G1 and G2 gratings. An exemplar system is shown in FIG. 3, where typically G0 and G2 are absorber gratings and G1 is a phase grating. The source grating G0, can be used to make radiation from the source more coherent but is not always necessary, and gratings G1 and G2 are normally termed phase and analyzer gratings. Subsequently, one of the two gratings G1 or G2 is moved perpendicular to the grating lamellae relative to the other gratings in a number of steps (so-called stepping), and if the source grating G0 is utilized it can be this grating that is stepped laterally (where laterally means perpendicular to the grating direction). Thereby, for each new grating position an image is recorded. Comparison of the image sequence acquired with and without a sample in the beam, allows to calculate the three imaging signals: transmission or attenuation (conventional X-ray image), phase-contrast image, and dark-field image. These gratings generate a fringe pattern on top of the conventional transmission image, and for example the dark-field signal is calculated as the loss of contrast of this fringe pattern. The fringe-pattern, which is analyzed in DAX and gbPC imaging, is a fine structure in the micrometer range. Using an analyzer grating with the same periodicity, a Moiré-pattern can be measured with the detector. Any movement of one or more interferometer components, such as the analyzer grating, in this length scale changes the phase of the Moiré-pattern.

Thus, a sample, the body in FIG. 3, modulates attenuation, refraction, and small angle scattering information onto the radiation. To separate phase information from other contributions to the signal, such as attenuation by the sample, inhomogeneous illumination or imperfections of the gratings, a phase-"stepping" approach is utilized. One of the gratings (either G1 or G2—or G0 if present) is scanned along the transverse direction over at least one period of the grating, and for every point of the scan an image is taken. The resultant phase-contrast, dark-field, and attenuation data then oscillates sinusoidal, with and without the sample, and this can be utilized to determine the dark-field, phase-contrast and attenuation images. Further detail on the standard phase stepping approach can be found in the paper by Weitkamp et al, Optics Express, Vol. 13, No. 16, (2005) 6296-6304.

Considering an implementation of a DAX and gbPC system in a commercial, clinical system, the handling and the cost for G2 are very critical. Handling will be difficult due to its large size, which will typically be of the order 43 cm squared, in particular if the system is not designed as a DAX-only system. Furthermore, when G2 is removed for standard X-ray imaging, as made clear from the above discussion it has to be brought back into exactly the same position, with an accuracy of about 1 µm, for DAX/gbPC imaging. Finally, it is a general disadvantage of G2 that it absorbs roughly half of the photons behind the patient, thus the dose efficiency is reduced.

WO2017/212000A1 provided a way to overcome these issues. This described an analyzing grid for phase-contrast imaging and/or dark-field imaging, a detector arrangement for phase-contrast imaging and/or dark-field imaging comprising such analyzing grid, an X-ray imaging system comprising such detector arrangement, a method for manufacturing such analyzing grid, a computer program element for controlling such analyzing grid or detector arrangement for performing such method and a computer readable medium having stored such computer program element. The analyzing grid comprises a number of X-ray converting gratings. The X-ray converting gratings are configured to convert incident X-ray radiation into light or charge. The number of X-ray converting gratings comprises at least a first X-ray converting grating and a second X-ray converting grating. Further, the X-ray converting gratings each comprise an array of grating bars, wherein the grating bars within each X-ray converting grating are arranged mutually displaced from each other in a direction perpendicular to the incident X-ray radiation by a specific displacement pitch. Further, the grating bars of the first X-ray converting grating are arranged mutually displaced from the grating bars of the second X-ray converting grating in the direction perpendicular to the incident X-ray radiation by the displacement pitch divided by the number of X-ray converting gratings. Thus, a detector design was provided where two interleaved detector channels are used, each forming a grating with the period of the fringe pattern. This concept, however, has the practical limitation that there is a certain amount of crosstalk between the channels, which reduces the fringe visibility. This crosstalk is hard to avoid since on one hand, there is need for a thick conversion layer, and on the other hand, the structure size of the interleaved channels is only in the order of a few 10 µm. Also, in certain situations noise in dark-field and phase-contrast imaging can be greater than that desired.

There is a need to address these issues.

SUMMARY OF THE INVENTION

It would be advantageous to have an improved detector for a dark-field, phase-contrast interferometric imaging system, and could also have utility for attenuation image data acquisition. The object of the present invention is solved with the subject matter of the independent claims, wherein further embodiments are incorporated in the dependent claims. It should be noted that the following described aspects and examples of the invention apply also to the detector for a dark-field and/or phase-contrast interferometric imaging system as well as to the X-ray imaging system having such a detector.

In a first aspect, there is provided a detector for a dark-field and/or phase-contrast interferometric imaging system, the detector comprising:

a plurality of pixels,
a plurality of first detector arrays;
a plurality of second detector arrays; and
a processing unit.

The plurality of pixels are arranged in a two-dimensional pattern. Each pixel comprises a first detector array and a second detector array. Each first detector array comprises a plurality of fingers. Each second detector array comprises a plurality of fingers. For each pixel the fingers of the first detector array are interleaved alternately with the fingers of the second detector array. For each pixel interaction with an incident X-ray photon can lead to charge generation in at least one finger of the first detector array of that pixel and can lead to charge generation in at least one finger of the second detector array of that pixel. For each pixel the first detector array is configured to detect a cumulative charge associated with the plurality of fingers of the first detector array and the second detector array is configured to detect a cumulative charge associated with the plurality of fingers of the second detector array. For each pixel the processing unit is configured to assign an X-ray interaction event to either the first detector array or the second detector array on the basis of the detector array that has the highest cumulative charge.

In other words, a detector is provided that can replace the G2 grating and the associated separate detector of a dark-field and phase-contrast interferometric imaging system, and where the effect of cross-talk caused by charge sharing and K-fluorescence that leads to a reduction in fringe visibility is mitigated.

Thus, a pure photon counting detector is provided where the X-ray photons are assigned to one or other of the arrays of pixels of the detector.

To understand this further, the operation of a standard X-ray Talbot-Lau interferometer needs to be considered. In such a system, a fringe pattern is generated at the position of the detector. This fringe pattern is basically a magnified image of the G1 grating, i.e. the fringe pattern is a grating-like periodically varying pattern of X-ray intensity. Changes in this fringe pattern with respect to its amplitude, phase, and mean intensity carries the desired information about the object, where movement of one of the gratings leads to a sinusoidal variation in intensity that can be used to reconstruct the information about the object. However, the period of the interference pattern is too small to be resolved with standard X-ray detector technology. This is why in standard systems the fringe pattern is in effect de-modulated by using an absorbing G2 grating in front of the detector. In order to operate the interferometer, the period of G2 must match the period of the fringe pattern. As discussed above, in a standard system movement of one of the gratings perpendicular to the grating orientation is carried out, for example the G2 grating, in order that the fringe pattern moves with respect to the G2 grating, and measurements are taken for instance at 0, 90, 180 and 270 degrees phase points of the sinusoidal intensity variation.

However, in the new development now there is no need for a G2 grating, with the detector itself having a structure, the fingers of the first and second detector arrays, that can match the period of the fringe pattern at the detector. Thus, again individual pixels of the detector can be too large to resolve the fringe pattern projected onto the detector. However, when the interferometric system is set up such that the period of each of the fingers of the detector arrays matches the period of the fringe pattern, then the required sinusoidal intensity variation can be extracted as the fringe pattern is moved laterally across the detector. Again, this can be either through movement of the detector laterally or lateral movement of the G1 grating or indeed both, or G0 if present. In effect, with this lateral movement the fringe peaks can at one position lead to a maximum of charge generation centred at the fingers of the first detector array of a pixel, with the fringe troughs leading to a lower charge generation centred at the fingers of the second detector array. Then as the fringe pattern moves laterally across the detector at a second position the roles are reversed and the peaks in charge are associated with the fingers of the second detector array of the same pixel of the detector. In effect the system acquires data that would have been acquired by a standard G2 grating based system at 0 degrees and 180 degrees, however it has been established that this can still be used to reconstruct the required information about the object.

The detector can be a photon counting detector.

In an example, for each pixel the processing unit is configured to assign the cumulative charge detected by the first detector array and the cumulative charge detected by the second detector array to either the first detector array or the second detector array on the basis of the detector array that has the highest cumulative charge.

In this manner, not only can it be determined which array to assign an x-ray interaction event to, but the energy associated with that event can be assigned thereby providing an energy resolving photon counting detector.

Thus, the system further increases signal and at the same time decrease noise by assigning all the charge to either one array of the other on the basis of the cumulative signals for each array to account for the intermediate positions between the two discussed "aligned" positions.

In an example, a direct conversion substrate is associated with each pixel.

Thus, the detector is a direct conversion photon counting detector, where an appropriately placed material leads to charge generation that can be collected or detected by the first and second detector arrays, which are in effect electrodes.

In an example, the processing unit is configured to assign the X-ray interaction event to either the first detector array or the second detector array when a difference between the cumulative charge detected by the first detector array and the cumulative charge detected by the second detector array is greater than a threshold.

In this manner, the effect of statistical or shot noise is mitigated, because the cumulative charge will only be assigned to one detector error when it can definitely be determined that this is the case taking noise into consideration.

In an example, the processing unit is configured to assign the cumulative charge detected by the first detector array and the cumulative charge detected by the second detector array to either the first detector array or the second detector array when a difference between the cumulative charge detected by the first detector array and the cumulative charge detected by the second detector array is greater than a threshold.

In an example, the processing unit is configured to discard the cumulative charge detected by the first detector array and the cumulative charge detected by the second detector array when the difference between the cumulative charge detected by the first detector array and the cumulative charge detected by the second detector array is less than or equal to a threshold.

Thus, in a dark-field and/or phase-contrast mode of operation when it cannot be determined in a statistically significant manner, whether the peaks of the fringes were at locations associated with the fingers of the first detector array or the fingers associated with the second detector array, the signal is not used.

In this way, noise can be reduced that would otherwise create a DC background that is not desired for dark-field and phase-contrast imaging.

In an example, in an attenuation mode of operation the processing unit is configured to assign the X-ray interaction event to either the first detector array or the second detector array when a difference between the cumulative charge detected by the first detector array and the cumulative charge detected by the second detector array is less than or equal to a threshold In an example, in an attenuation mode of operation the processing unit is configured to assign the cumulative charge detected by the first detector array and the cumulative charge detected by the second detector array to either the first detector array or the second detector array when a difference between the cumulative charge detected by the first detector array and the cumulative charge detected by the second detector array is less than or equal to a threshold.

In this manner, the signals need not be used for dark-field or phase-contrast imaging and provide for attenuation image data, where the signal can be maximised at increased resolution.

In an example, each finger of the first detector array has a width of 10-20 μm and each finger of the second detector array has a width of 10-20 μm.

In an example, the fingers of the first detector array have the same width as the fingers of the second detector array.

In an example, the fingers of the first detector array have a different width to the fingers of the second detector array.

In an example, the first detector array of each pixel comprises 3 or 5 fingers and the second detector array of each pixel comprises an equivalent number of fingers.

In an example, each pixel has a width of 154 μm.

In an example, each pixel has a breadth perpendicular to the width of 154 μm.

Thus, the pixels of the detector can be standard 154 μm square pixels.

In a second aspect, there is provided an X-ray imaging system, comprising:
an X-ray source;
an interferometric arrangement; and
a detector (10) according to the first aspect.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
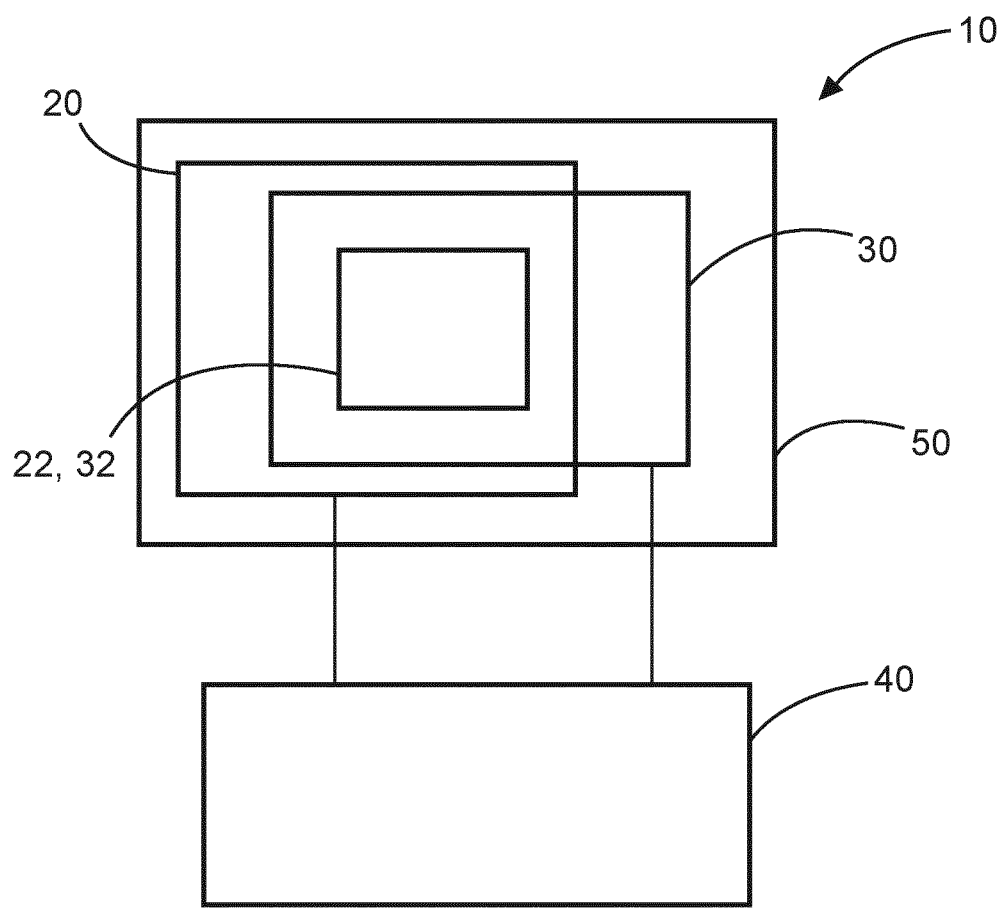
FIG. 1 shows a schematic set up of an example of a new detector for a dark-field, phase-contrast and attenuation interferometric imaging system.

FIG. 1 shows an example of a detector 10 for a dark-field and/or phase-contrast interferometric imaging system. The detector 10 comprises a plurality of pixels 50, a plurality of first detector arrays 20, a plurality of second detector arrays 30, and a processing unit 40. The plurality of pixels are arranged in a two-dimensional pattern. Each pixel comprises a first detector array and a second detector array. Each first detector array comprises a plurality of fingers 22. Each second detector array comprises a plurality of fingers 32. For each pixel the fingers of the first detector array are interleaved alternately with the fingers of the second detector array. For each pixel interaction with an incident X-ray photon can lead to charge generation in at least one finger of the first detector array of that pixel and can lead to charge generation in at least one finger of the second detector array of that pixel. For each pixel the first detector array is configured to detect a cumulative charge associated with the plurality of fingers of the first detector array and the second detector array is configured to detect a cumulative charge associated with the plurality of fingers of the second detector array. For each pixel the processing unit is configured to assign an X-ray interaction event to either the first detector array or the second detector array on the basis of the detector array that has the highest cumulative charge.

In an example, the detector is suitable to determine attenuation image data.

In an example, the plurality of fingers of the plurality of first detector arrays are substantially parallel to each other.

In an example, the plurality of fingers of the plurality of second detector arrays are substantially parallel to each other.

In an example, the plurality of fingers of the plurality of first detector arrays are substantially parallel to the plurality of fingers of the plurality of second detector arrays.

When the detector is used in a system, the detector will be oriented relative to the X-ray source such that for each pixel the fingers of the first detector array are interleaved alternately with the fingers of the second detector array in a direction perpendicular to incident X-rays.

According to an example, for each pixel the processing unit is configured to assign the cumulative charge detected by the first detector array and the cumulative charge detected by the second detector array to either the first detector array or the second detector array on the basis of the detector array that has the highest cumulative charge.

According to an example, a direct conversion substrate is associated with each pixel.

In an example, the direct conversion substrate is on top of the first and second detector arrays with respect to a direction from which X-rays will interact with the detector.

According to an example, the processing unit is configured to assign the X-ray interaction event to either the first detector array or the second detector array when a difference between the cumulative charge detected by the first detector array and the cumulative charge detected by the second detector array is greater than a threshold.

In an example, the threshold is an absolute threshold.

In an example, the threshold is determined relative to the cumulative charge of the two detector arrays. For example, the threshold can relate to a square root of the cumulative charge detected.

According to an example, the processing unit is configured to assign the cumulative charge detected by the first detector array and the cumulative charge detected by the second detector array to either the first detector array or the second detector array when a difference between the cumulative charge detected by the first detector array and the cumulative charge detected by the second detector array is greater than a threshold.

According to an example, the processing unit is configured to discard the cumulative charge detected by the first detector array and the cumulative charge detected by the second detector array when the difference between the cumulative charge detected by the first detector array and the cumulative charge detected by the second detector array is less than or equal to a threshold.

According to an example, in an attenuation mode of operation the processing unit is configured to assign the X-ray interaction event to either the first detector array or the second detector array when a difference between the cumulative charge detected by the first detector array and the cumulative charge detected by the second detector array is less than or equal to a threshold.

According to an example, in an attenuation mode of operation the processing unit is configured to assign the cumulative charge detected by the first detector array and the cumulative charge detected by the second detector array to either the first detector array or the second detector array when a difference between the cumulative charge detected by the first detector array and the cumulative charge detected by the second detector array is less than or equal to a threshold.

According to an example, each finger of the first detector array has a width of 10-20 µm and each finger of the second detector array has a width of 10-20 µm.

In an example, each finger of the first detector array has a width of 5-10 µm.

In an example, each finger of the second detector array has a width of 5-10 µm.

In an example, each finger of the first detector array has a width of 20-30 µm.

In an example, each finger of the second detector array has a width of 20-30 µm.

According to an example, the fingers of the first detector array have the same width as the fingers of the second detector array.

According to an example, the fingers of the first detector array have a different width to the fingers of the second detector array.

In an example, a duty cycle of the fingers of the detector arrays is 40%.

In this manner, it has been found that signal to noise can be increased above that for an arrangement having a 50% duty cycle.

In an example, the duty cycle is 47.5%.
In an example, the duty cycle is 45%.
In an example, the duty cycle is 42.5%.
In an example, the duty cycle is 37.5%.
In an example, the duty cycle is 35%.
In an example, the duty cycle is 32.5%.
In an example, the duty cycle is 30%.

It is to be noted that the duty cycle can be a real duty cycle, based on the geometry of the fingers of the arrays, having for example different widths. However, the duty cycle can also be considered to be an effective duty cycle where operation of the new detector can in effect lead to a reduction in duty cycle as a consequence of its operation, thereby providing for the advantages of a reduced duty cycle of less than 50% for a structure that actually has a physical duty cycle arrangement of 50%.

In an example, the plurality of pixels are arranged in a 2D rectangular or square grid.

According to an example, the first detector array of each pixel comprises 4 or 5 fingers and the second detector array of each pixel comprises an equivalent number of fingers.

According to an example, each pixel has a width of 154 µm.

According to an example, each pixel has a breadth perpendicular to the width of 154 µm.

In an example, a length of each finger is substantially greater than its width.

Figure 2:
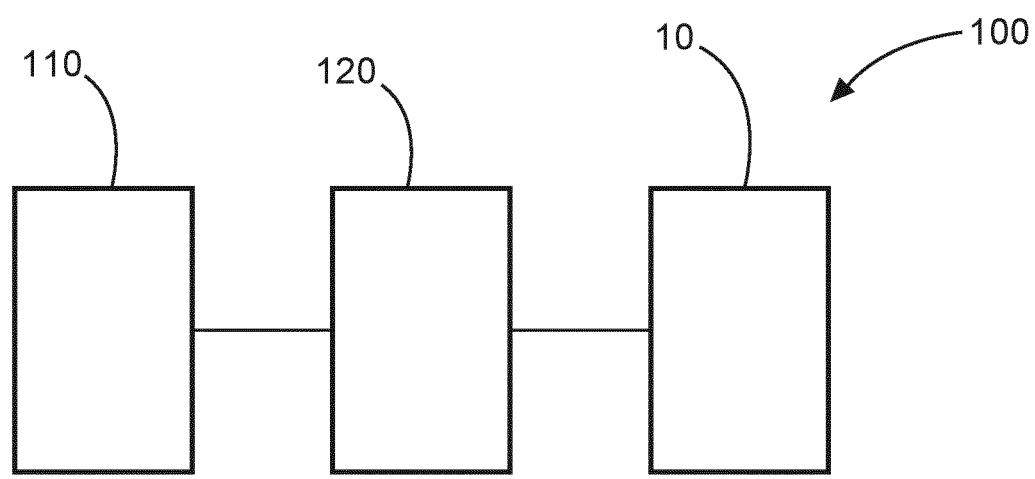
FIG. 2 shows a schematic set up of an example of an X-ray imaging system with a new detector for a dark-field, phase-contrast and attenuation interferometric imaging system.
Figure 3:
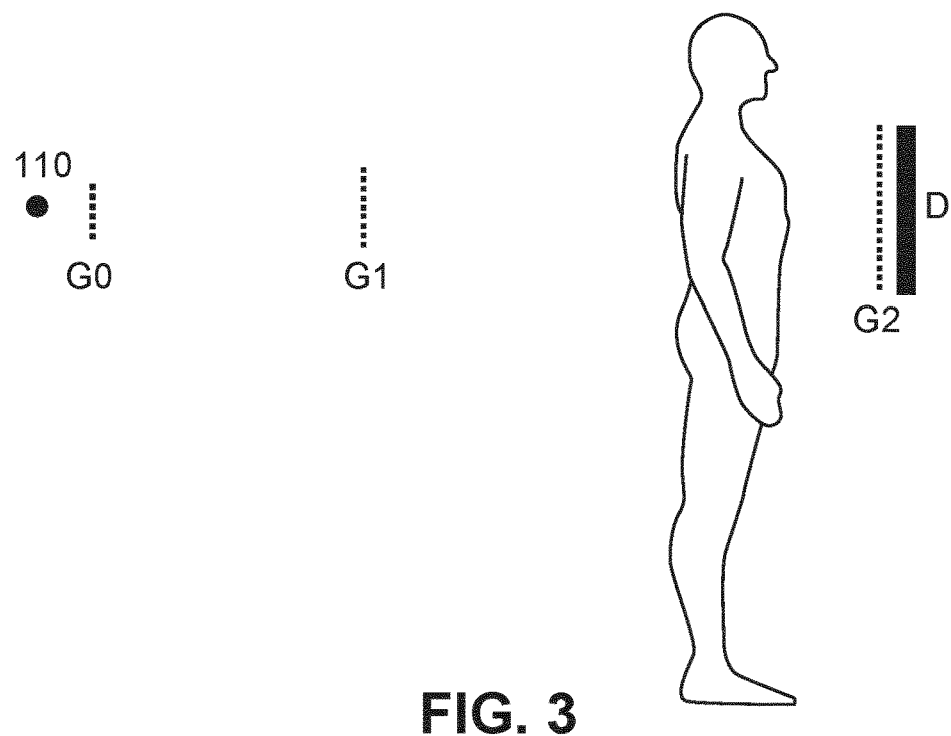
FIG. 3 shows a schematic example of a standard dark-field and phase-contrast imaging system, with an X-ray source, G0, G1 and G2 gratings, and an X-ray detector.

FIG. 2 shows an example of an X-ray imaging system 100. The X-ray imaging system 100 comprises an X-ray source 110, an interferometric arrangement 120, and a detector 10 as described with respect to FIG. 1.

The detector for a dark-field, phase-contrast interferometric imaging system that can also acquire and attenuation image data and the X-ray imaging system having such a detector are now described with respect to specific embodiments, where reference is made to FIGS. 4-7.

Figure 4:
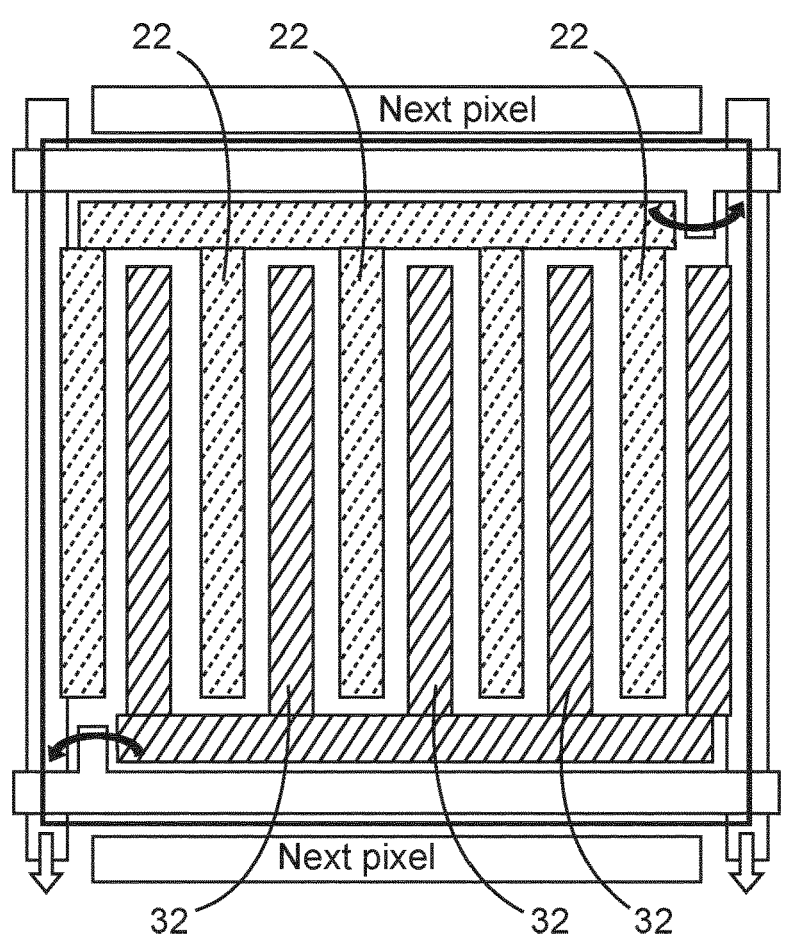
FIG. 4 shows a schematic illustration of a pixel design as viewed from the top, where a number of such pixels form the new detector for a dark-field, phase-contrast and attenuation interferometric imaging system.

FIG. 4 shows a schematic illustration of a pixel design as viewed from the top. Only one pixel 50 is shown of the detector, where the pixel has two detector arrays 20 and 30, with associated fingers or electrodes 22 and 32, however the detector has many such pixels laid out in a two-dimensional grid. A direct conversion material is utilized along with a pulse counting frontend. To conveniently match existing technologies, the basic pixel geometry is similar to a standard X-ray detector with 154 µm pixel size and with gate and readout lines. Thus, it will be appreciated that a complete detector will have many such pixels as shown in FIG. 4, but arranged in a 2D grid to cover a required detector area. Each pixel is the same as, and oriented in the same manner as shown in FIG. 4, and X-ray interaction is perpendicular to the structure shown—thus into the page.

The pixel structure, of a standard X-ray detector, is however modified to provide the structure shown in FIG. 4 so that two sub-pixel electrodes (also called detector arrays 20 and 30 having fingers) per 154 µm pixel 50 can be read out independently. In the example shown in FIG. 4 there are two gate lines instead of one so that the two electrode structures (a first detector array having fingers and a second detector array having fingers) within the pixel can be read out one after the other. Alternatively, there could be one gate line but two readout lines per pixel so that the two electrode structures (fingers) could be read out simultaneously.

The comb-like interleaved electrodes (fingers) 22 and 32 have a structure size of the order of 10-20 µm. As an example, there could be five fingers down and five fingers up, with a pitch of 15.4 µm, to be compatible with the standard pixel size of 154 µm used in standard X-ray detectors. Alternatively, there could be four fingers down and four fingers up with a pitch of 19.25 μm. For DAX and gbPC imaging the pitch of the interleaved finger electrodes is uninterrupted across different detector pixels.

Figure 5:
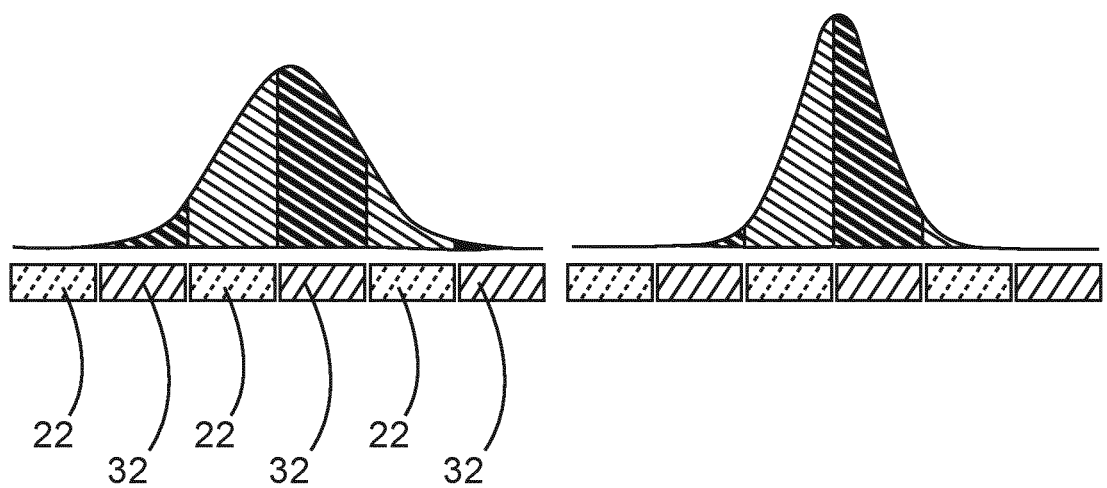
FIG. 5 shows schematic illustrations of total charge in adjacent fingers of a first detector array and a second detector array of a pixel of a new detector for a dark-field, phase-contrast and attenuation interferometric imaging system.
Figure 6:
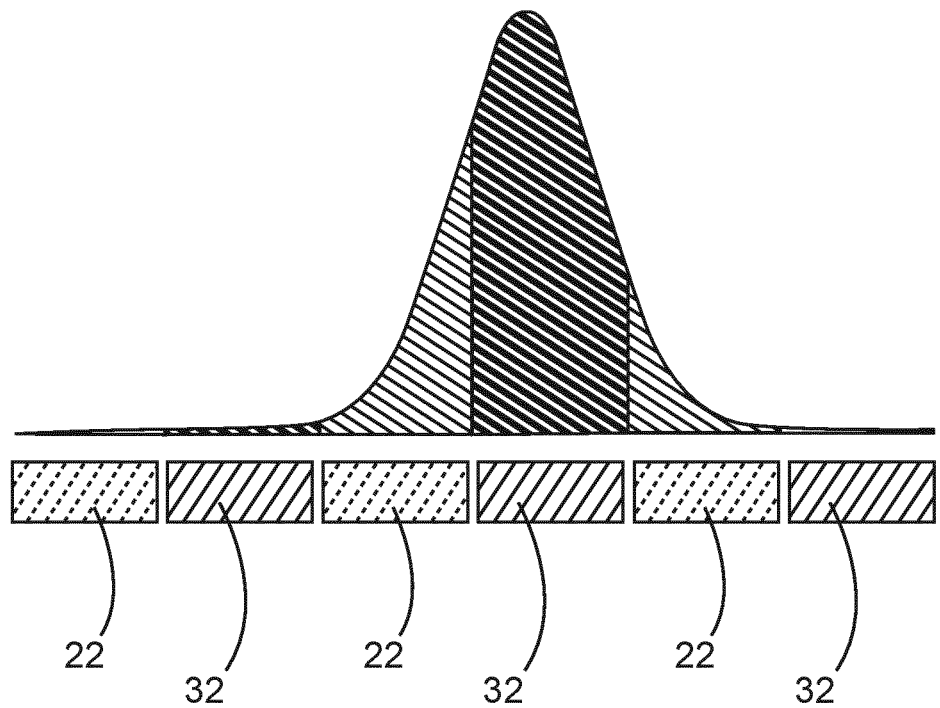
FIG. 6 shows a schematic illustration of total charge in adjacent fingers of a detector for a dark-field, phase-contrast and attenuation interferometric imaging system.

A representative signal distribution across the finger electrodes 22 and 32 of the two channels or arrays 20 and 30 is illustrated in FIGS. 5 and 6, where for simplicity there is only one X-ray interaction event shown. The charge cloud spreads to the electrodes as it travels from the point where the photon was absorbed by the direct absorption material and charge was generated. Thus, the charge cloud it will cover several of the electrode lines (fingers). This effect is known as pulse sharing in photon counting detector technology. Simulation has shown that a homogeneously charged sphere with 15 μm radius in case of a 0.5 mm thick detector layer is to be expected. It is to be noted that when the detector is used in the interferometric arrangement, replacing the G2 absorption grating and the associated detector, there will actually also be a fringe pattern projected at the surface of the detector, where the interferometric system will be set up such that a fringe period equals the period of the fingers of each of the detector arrays—in analogy to the period of the G2 grating matching the fringe period.

As shown in FIG. 5 charge can be relatively uniformly spread across electrodes (fingers). This can happen if the charge cloud is very broad or the initial event (i.e. the conversion of the photon in a charge cloud) occurred close to the boundary between fingers.

In the new design, pulses are detected simultaneously (in coincident mode) in the two channels and their height (e.g. their total energy) is compared. Thus, all the charge in the first detector array 20 collected by all the fingers 22 is accumulated, and all the charge in the second detector array 30 collected by all the fingers 32 is accumulated. The total energy in one array can be compared against the total energy in the other array. Assignment of the X-ray interaction event to one or other of the arrays can be carried out based on which array had the highest cumulative charge providing for a pure photon counting system. However, assignment of all the energy from both arrays or channels to one of the channels (the first detector array 20 or the second detector array 30) can also be undertaken, based on the channel/array that has the highest signal, thereby providing for an energy resolving photon counting mode. As shown in the FIG. 6 in certain situations the determination of which array to which the event and/or energy is to be assigned is quite clear, where the fingers of one detector array of a pixel clearly collect more charge than the fingers of the other detector array of the pixel. However, as shown in FIG. 5 the situation can become complicated. One has to recall, that the fringe pattern generated by the G1 grating is projected onto the new detector and those fringes will move sideways, where the fringes have a period equal to that of the fingers of each detector array. Therefore, necessarily a peak of a fringe will generate charge centred on the fingers of one detector array, where with movement of the fringes the peak of that fringe will move to the generate charge centred on the fingers of the other detector array of a pixel. Thus, at some point the accumulated charge for each array would be the same, discounting noise, and with noise there is a range over which assignment to one channel or the other is difficult. The situation is further complicated due to charge spreading out from a single x-ray interaction event as discussed above. In other words, assignment to a particular channel suffers strongly from noise if the pulses in the two channels are very similar in height, where due to shot noise all the charge could actually be assigned to the wrong channel. This can happen if the charge cloud is very broad or the initial event (i.e. the conversion of the photon in a charge cloud) occurred close to the boundary of the channels, and as discussed is expected to happen more frequently at certain fringe pattern to detector positions. This sensitivity to noise implies that these type of events will mainly create a DC background that is not desired for dark-field/phase-contrast (DAX/gbPC imaging).

Thus, pulses are detected simultaneously (in coincident mode) in the two channels and their height (e.g. their total energy) is compared. Then, the energy difference is determined and the following cases are handled:

if the difference between the pulses is larger than a threshold, the total energy is assigned to the channel (one of the two detector arrays 20 or 30 of a pixel 50) with the larger pulse;

if the difference between the pulses is equal to or lower than the threshold, the total energy is either discarded or assigned to a third channel that will be used subsequently only for the generation of the attenuation image.

In an alternative embodiment, there is no absolute threshold, but a threshold relative to the total energy of the two pulses.

In that way every absorption event can be attributed to the correct detector array, independent of charge sharing, within one detector pixel. To account for absorption events near the edge of a pixel, coincident signals of neighbouring pixels are compared and if they would lead to noise in gbPC/DAX imaging they are discarded, but can be made use of when constructing the attenuation image.

Figure 7:
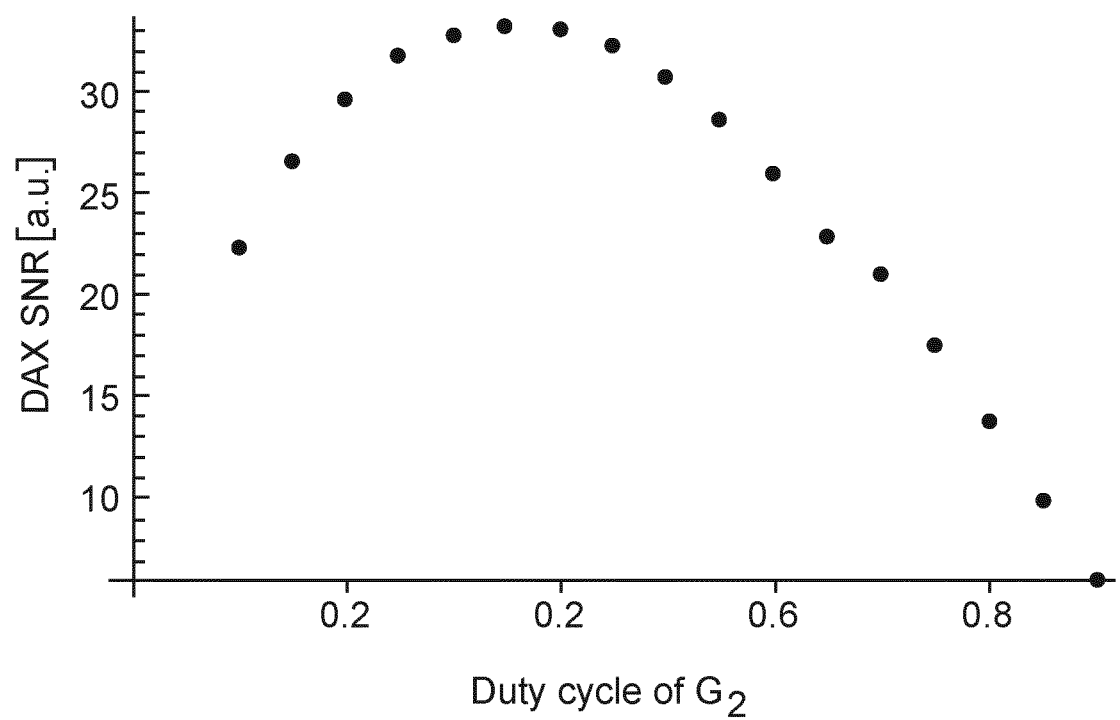
FIG. 7 shows signal to noise level in arbitrary units as a function of the duty cycle of G2.

FIG. 7 shows signal to noise level in arbitrary units as a function of the duty cycle of $G_2$. This show that the signal to noise ratio (SNR) of DAX/gbPC can be improved by reducing the duty cycle of $G_2$, where the same situation applied analogously to the fingers of the detector arrays of a pixel. It is to be noted that reducing the duty cycle improves the SNR of the DAX (and the phase-contrast image) but it decreases the SNR of the attenuation image since more photons are discarded in the first place. This effect can be explained in more detail as follows. In a "conventional" dark-field/phase-contrast X-ray system with an absorbing $G_2$, the attenuation and the dark-field images have competing interests. If one considers the attenuation images, then the $G_2$ grating does not help you at all, it just reduces the number of photons being detected and thus is reduces SNR. If one considers the dark-field image, it is a bit more complex, because one wants to measure the amplitude and the mean of a sine-like signal. For amplitude, one has to be aware that the period of the signal matches the grating period. For 50% duty cycle, basically a box-car low-pass filter is applied to the signal before it is sampled. The low-pass filtering reduces the amplitude of the signal to be measured, so there is a desire to reduce the duty cycle in order to reduce the effect of low-pass filtering. Of course, at the same time, the number of photons is reduced, thus increasing the noise. FIG. 7 shows a simulation result that the best trade-off is to use a $G_2$ grating with approximately 40% duty cycle. Thus, in the new detector design that virtually creates a G2/detector combination, by discarding pulses with similar height (within a threshold), the duty cycle of the two channels is effectively reduced, resulting in an improved SNR of the dark-field and phase-contrast images while maintaining the dose efficiency of the attenuation image. In addition to generating this duty cycle by through away charge in certain situations, the actual structure of the fingers of the two detector arrays of a pixel can be modified to have a duty cycle other than 50%, thereby also providing for an improvement in signal to noise.

This new detector for DAX/gbPC thus has counting detectors with two arrays of electrodes (fingers) per 154 μm square detector pixel. In a specific embodiment, this pixel size is 10.5× smaller than the 0.5 mm square pixel used in spectral CT. This enables use of detector materials that have a 10× lower mobility than the CZT detectors in the spectral CT concept. Perovskites, especially methyl amine lead iodide (MA-$PbI_3$), are suitable for this counting DAX/gbPC detector.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A detector for a dark-field and/or phase-contrast interferometric imaging system, the detector comprising:
   a plurality of pixels;
   a plurality of first detector arrays;
   a plurality of second detector arrays; and
   a processor;
   wherein the plurality of pixels are arranged in a two-dimensional pattern;
   wherein each pixel comprises a first detector array and a second detector array;
   wherein each first detector array comprises a plurality of fingers;
   wherein each second detector array comprises a plurality of fingers;
   wherein for each pixel, the fingers of the first detector array are interleaved alternately with the fingers of the second detector array;
   wherein for each pixel, interaction with an incident X-ray photon can lead to charge generation in at least one finger of the first detector array of that pixel and can lead to charge generation in at least one finger of the second detector array of that pixel;
   wherein for each pixel, the first detector array is configured to detect a cumulative charge associated with the plurality of fingers of the first detector array and the second detector array is configured to detect a cumulative charge associated with the plurality of fingers of the second detector array; and
   wherein for each pixel, the processor is configured to assign an X-ray interaction event to either the first detector array or the second detector array on the basis of the detector array that has the highest cumulative charge.

2. The detector according to claim 1, wherein, for each pixel, the processor is configured to assign the cumulative charge detected by the first detector array and the cumulative charge detected by the second detector array to either the first detector array or the second detector array on the basis of the detector array that has the highest cumulative charge.

3. The detector according to claim 1, wherein a direct conversion substrate is associated with each pixel.

4. The detector according to claim 1, wherein the processor is configured to assign the X-ray interaction event to either the first detector array or the second detector array when a difference between the cumulative charge detected by the first detector array and the cumulative charge detected by the second detector array is greater than a threshold.

5. The detector according to claim 4, wherein the processor is configured to discard the cumulative charge detected by the first detector array and the cumulative charge detected by the second detector array when the difference between the cumulative charge detected by the first detector array and the cumulative charge detected by the second detector array is less than or equal to a threshold.

6. The detector according to claim 1, wherein the processor is configured to assign the cumulative charge detected by the first detector array and the cumulative charge detected by the second detector array to either the first detector array or the second detector array when a difference between the cumulative charge detected by the first detector array and the cumulative charge detected by the second detector array is greater than a threshold.

7. The detector according to claim 1, wherein in an attenuation mode of operation the processor is configured to assign the X-ray interaction event to either the first detector array or the second detector array when a difference between the cumulative charge detected by the first detector array and the cumulative charge detected by the second detector array is less than or equal to a threshold.

8. The detector according to claim 1, wherein in an attenuation mode of operation the processor is configured to assign the cumulative charge detected by the first detector array and the cumulative charge detected by the second detector array to either the first detector array or the second detector array when a difference between the cumulative charge detected by the first detector array and the cumulative charge detected by the second detector array is less than or equal to a threshold.

9. The detector according to claim 1, wherein each finger of the first detector array has a width of 10-20 μm and each finger of the second detector array has a width of 10-20 μm.

10. The detector according to claim 1, wherein the fingers of the first detector array have the same width as the fingers of the second detector array.

11. The detector according to claim 1, wherein the fingers of the first detector array have a different width to the fingers of the second detector array.

12. The detector according to claim 1, wherein the first detector array of each pixel comprises 4 or 5 fingers and the second detector array of each pixel comprises an equivalent number of fingers.

13. The detector according to claim 1, wherein each pixel has a width of 154 μm.

14. The detector according to claim 1, wherein each pixel has a breadth perpendicular to the width of 154 μm.

15. An X-ray imaging system, comprising:
an X-ray source;
an interferometric arrangement; and
a detector for a dark-field and/or phase-contrast interferometric imaging system, the detector comprising:
a plurality of pixels;
a plurality of first detector arrays;
a plurality of second detector arrays; and
a processor;
wherein the plurality of pixels are arranged in a two-dimensional pattern;
wherein each pixel comprises a first detector array and a second detector array;
wherein each first detector array comprises a plurality of fingers;
wherein each second detector array comprises a plurality of fingers;
wherein for each pixel, the fingers of the first detector array are interleaved alternately with the fingers of the second detector array;
wherein for each pixel, interaction with an incident X-ray photon can lead to charge generation in at least one finger of the first detector array of that pixel and can lead to charge generation in at least one finger of the second detector array of that pixel;
wherein for each pixel, the first detector array is configured to detect a cumulative charge associated with the plurality of fingers of the first detector array and the second detector array is configured to detect a cumulative charge associated with the plurality of fingers of the second detector array; and
wherein for each pixel, the processor is configured to assign an X-ray interaction event to either the first detector array or the second detector array on the basis of the detector array that has the highest cumulative charge.

* * * * *